United States Patent [19]
Haug

[11] Patent Number: 5,339,677
[45] Date of Patent: Aug. 23, 1994

[54] HYDRAULIC HOSE FLEX-IMPULSE TESTER

[75] Inventor: Thomas J. Haug, Manitowoc, Wis.

[73] Assignee: HMF, Incorporated, Manitowoc, Wis.

[21] Appl. No.: 119,270

[22] Filed: Sep. 9, 1993

[51] Int. Cl.$^5$ .................. G01N 3/12; G01N 3/32
[52] U.S. Cl. ........................... 73/49.5; 73/37; 73/812
[58] Field of Search ............ 73/49.5, 37, 794, 807, 73/812, 808

[56] References Cited

U.S. PATENT DOCUMENTS

| | | | |
|---|---|---|---|
| 1,494,350 | 5/1924 | Flinner | 73/37 |
| 1,512,063 | 10/1924 | Sproull | 73/49.5 |
| 1,608,067 | 11/1926 | Hull | 73/37 |
| 2,412,524 | 12/1946 | Mallory | |
| 2,657,573 | 11/1953 | Castricum | 73/37 X |
| 3,498,119 | 3/1970 | St. Jean et al. | 73/49.5 X |
| 3,621,711 | 11/1971 | Griffith et al. | 73/794 |

FOREIGN PATENT DOCUMENTS

| | | | |
|---|---|---|---|
| 279837 | 12/1991 | Japan | 73/49.5 |
| 203950 | 7/1992 | Japan | 73/37 |

*Primary Examiner*—Hezron E. Williams
*Assistant Examiner*—Joseph W. Roskos
*Attorney, Agent, or Firm*—Wheeler Law Firm

[57] ABSTRACT

A hydraulic hose impulse tester capable of simultaneously testing multiple samples of hydraulic hose in a stationary-impulse condition and in a flexing-impulse condition in the same test environment. The tester eliminates varying extraneous factors which can affect comparative test results by performing the static and dynamic tests simultaneously. Alternatively, all sample hoses can be tested in either a static or dynamic condition.

10 Claims, 2 Drawing Sheets

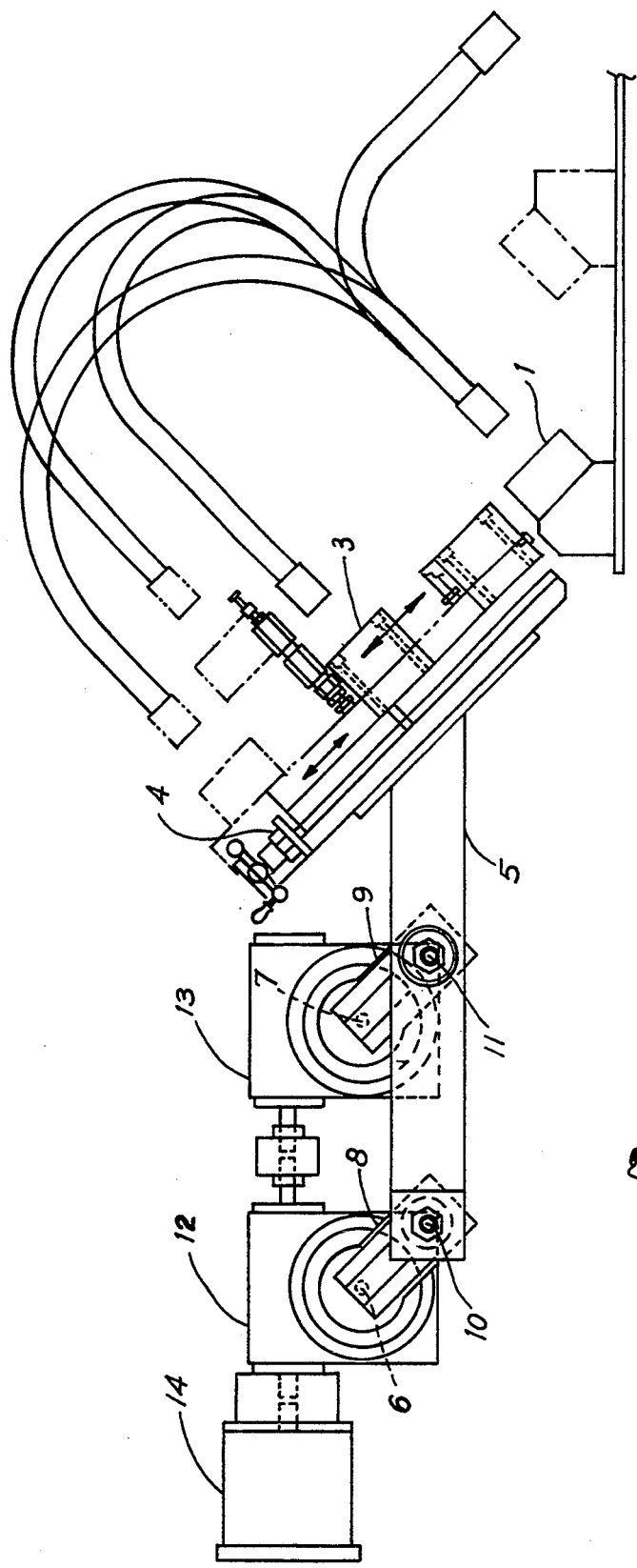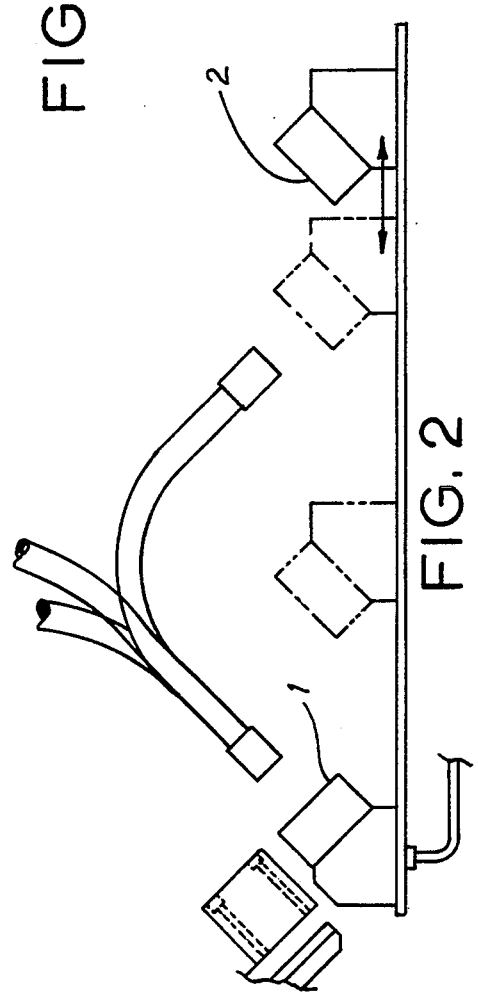
FIG.1
FIG.2

HYDRAULIC HOSE FLEX-IMPULSE TESTER

BACKGROUND OF THE INVENTION

In the past it has been difficult to test hydraulic hose reliably because the test procedure calls for sample hydraulic hose to be tested with high pressure impulses both while it is sitting still and while it is flexing. Before the invention of my hydraulic hose flex-impulse tester, this required testing on separate test apparatus. The first apparatus was designed only for stationary-impulse testing. The second apparatus was designed only for flex-impulse testing. Each apparatus required its own hydraulic oil tank, oil heater, and oil pump. If each apparatus was located in a different environment or if each test was performed at a different time, the atmospheric conditions for each test, including ambient temperature, were different. These disparate testing environments have the potential to significantly affect the test results.

My invention solves the above problems by combining the stationary-impulse and flex-impulse testing apparatus into one simplified unit. Fewer manifolds, and only one oil tank, oil heater, and oil pump are required for both the stationary-impulse and flex-impulse test. Because both tests are performed simultaneously in the same test chamber, the atmospheric conditions for each test are identical. More accurate test results are produced.

SUMMARY OF THE INVENTION

My invention has been designed to satisfy both the Society of Automotive Engineers stationary-impulse and flex-impulse test procedures on samples of the same hydraulic hose specimens. The procedures can be performed either separately or simultaneously. My testing device complies with the current SAE J343 Impulse Test and SAE J1405 Flex-Impulse Test procedures for hydraulic hose assemblies. These procedures establish a uniform method for comparative impulse testing of hydraulic hose assemblies with and without flexing in order to determine the effect of flexing on the ultimate life of the hydraulic hose.

An optimum test consists of cutting samples from a continuous length of hydraulic hose and subjecting alternate specimens to both flexing and non-flexing impulse tests simultaneously. As both tests can now be conducted simultaneously on the same machine, other variables such as oil temperature, impulse rate, wave form, and ambient temperature will also be identical insuring optimum validity of comparison. The present invention uses a unique and simple design that minimizes these variables so that a better and more accurate comparison of the same hose under flexing and non-flexing conditions is achieved.

The test chamber of my invention contains a tank, a tandem pump, a heater, a cooler, a check valve, an intensifier, an orbiter assembly, and three manifolds to which the test specimens are connected. A single inlet manifold, manifold 1, is the source of the heated liquid under pressure to which pressure pulses are applied. Manifold 1 has at least one inlet and multiple outlet ports. The inlet end of each sample hose to be tested is attached to an outlet port of manifold 1.

Manifold 2 is an outlet manifold and receives the outlet ends of some or all of the sample hoses at its multiple inlet ports for stationary-impulse testing. The inlet ports of manifold 2 are at a predetermined angle to the outlet ports of manifold 1. While manifold 2 remains stationary during testing, it is mounted on a slide such that its linear position with respect to manifold 1 is adjustable. The position of manifold 2 for testing is determined according to the length and diameter of the sample hoses to be tested. For example under the SAE J343 test specification, each hose must make a 90 degree bend between the outlet port of manifold 1 and the inlet port of manifold 2. Manifold 2 has at least one outlet port through which the heated liquid is returned to the tank.

Manifold 3 is the outlet manifold for the flex-impulse test and receives the outlet ends of some or all of the sample hoses at its multiple inlet ports, and is also mounted on a slide which in turn is mounted on a moving means. The moving means to which the slide of manifold 3 is attached is capable of moving manifold 3 in a continuous predetermined pattern. For example under the SAE J1405 test specification, a circular pattern of a predetermined radius positioned such that the center line of the inlet ports of manifold 3 remain parallel to the center line of the inlet ports of manifold 1 is specified. The slide is adjusted so that each sample hose interconnected between manifold 1 and manifold 3 cycles from a minimum to a maximum bend radius with each revolution of the moving means.

The moving means includes a link arm to which the slide of manifold 3 is attached at one end. Two crank arms rotate and drive the link arm in the predetermined path. One end of each crank arm is attached to the link arm; the first near the link arm's center and the second at the link arm's end opposite the slide. The length of each crank arm can be adjusted to increase or decrease the link arm's path of rotation. However, the lengths of each such arm must be equal if the link arm is to remain parallel to the base of the test chamber. The opposite ends of each crank arm are each connected to a reducer. The first reducer has an input to which a motor is attached and two independent outputs. The first output is attached to the first crank arm and the second output is coupled to the input of the second reducer. The second reducer has only one output to which the second crank arm is connected. Each reducer reduces the motor's speed of rotation and increases the motor's torque.

The motor speed is electronically controlled to satisfy the test requirements. When the motor is energized manifold 3 rotates in the predetermined path. Manifold 3 has at least one outlet port through which the liquid is returned to the tank.

Liquid to be pumped through each test hose is stored in the tank and heated to a predetermined temperature by the heater located between the tank and inlet manifold 1. During the low pressure non-impulse of the wave form, the low volume section of the tandem pump circulates the liquid into manifold 1, through the sample hoses, into either manifold 2 or 3, and back into the tank. If the liquid leaving manifold 2 or 3 is too hot, it is cooled by a heat exchanger located in the return line before the tank. During the high pressure impulse of the wave form the check valve stops low pressure circulation and pressure builds up to impulse test pressure as the intensifier is charged. When charging is complete, the high pressure impulse is discharged into manifold 1. The high pressure impulses occur at a predetermined cycle rate. The rotational speed of manifold 3 in revolutions per minute is equal to $36 \pm 2\%$ of the impulse rate of the liquid in cycles per minute.

Each manifold has a row of inlet or outlet ports to receive up to 6 sample hoses for testing purposes. A total of six hose samples may all be tested in the static predetermined angle mode or all in the dynamic predetermined path mode or three in each mode. The latter is particularly useful since samples of the same hose can be tested simultaneously under the same conditions. Ports not used during testing are plugged.

Accordingly, the present invention complies with all engineering test requirements while at the same time eliminating or substantially reducing the variables currently inherent with such test. This allows for extremely accurate results to be achieved quickly and easily.

DESCRIPTION OF THE DRAWINGS

FIG. 1 is a side elevational view of the Tester showing manifolds 1 and 3

FIG. 2 is a side elevational view of the Tester showing manifolds 1 and 2

DETAILED DESCRIPTION

Figure 3:
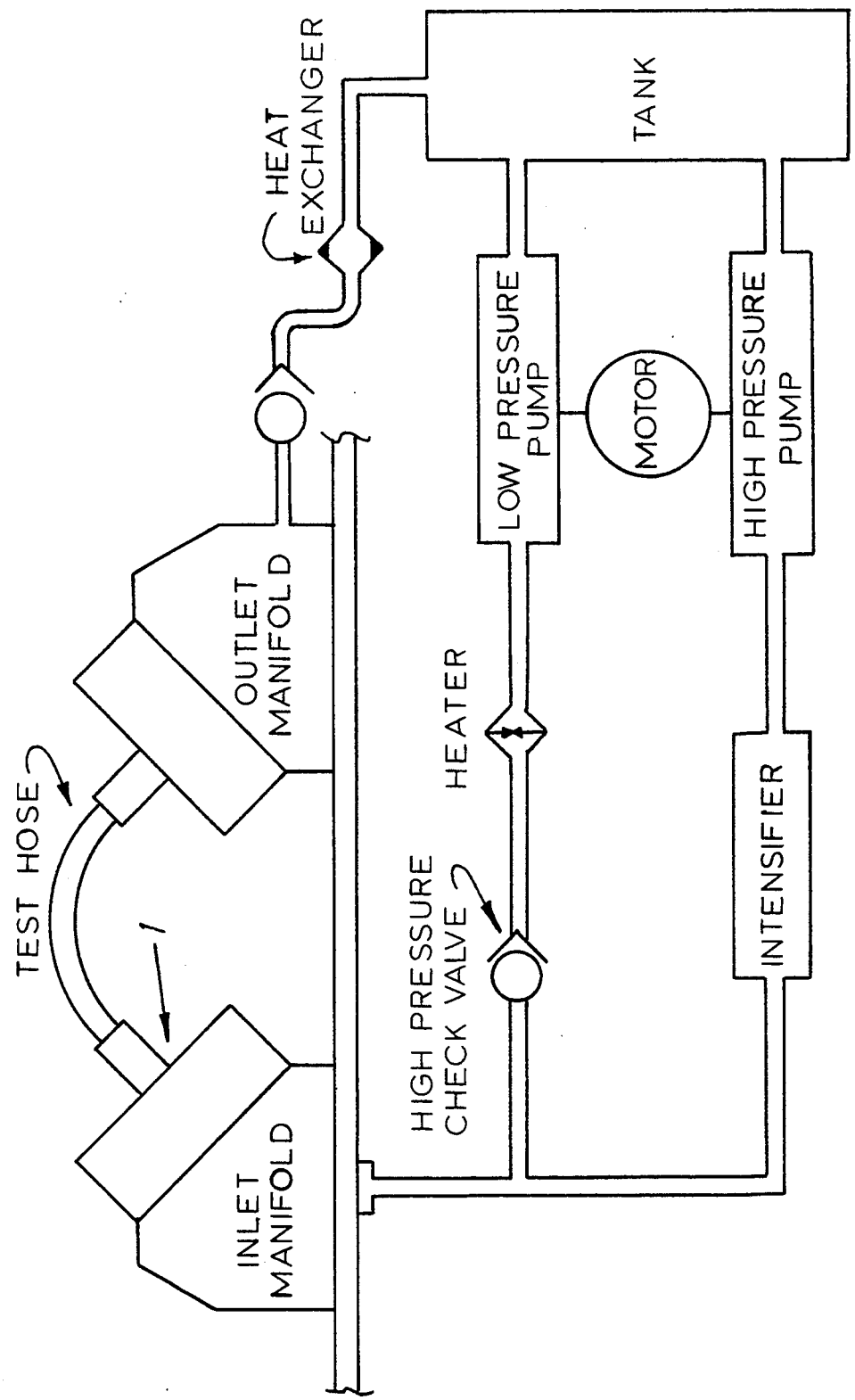
FIG. 3 is a schematic diagram of the hydraulic circuit of my Hydraulic Hose Flex-Impulse Tester.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

My invention has been designed to satisfy both the stationary-impulse and flex-impulse test procedures on samples of the same hydraulic hose specimens either separately or simultaneously. The testing device complies with the current SAE J343 Impulse Test and SAE J1405 Flex-Impulse Test procedures. An optimum test consists of cutting samples from a continuous length of hose and subjecting alternate specimens to both flexing and non-flexing impulse tests. As both tests can now be conducted simultaneously on the same machine, other variables such as oil temperature, impulse rate, wave form, and ambient temperature will also be identical insuring optimum test validity of comparison.

The test chamber of my invention, referred to hereafter as 100, contains three manifolds 1, 2, and 3, a base 80, a tank 20, a tandem pump 21 driven by a motor 50, a heater 22, a check valve 24, an intensifier 37, a heat exchanger 38, another check valve 39, an orbiter assembly 90 connected to a motor 14, and up to six sample test hoses 15. The tandem pump 21 has a high volume section 35 and a low volume section 36 as shown in FIG. 3. FIG. 3 is a schematic diagram of the hydraulic circuit of my invention. Hydraulic oil for performing the stationary-impulse and flex-impulsing test is stored in tank 20. The hydraulic oil is heated to a predetermined temperature by heater 22 as it is pumped from tank 20 into manifold 1 by the low volume section 36 of pump 21. High volume section 35 of Pump 21 charges the intensifier 37 which impulses the heated oil through the system at a predetermined impulse rate and wave form. During the high pressure impulse, check valve 24 stops low pressure circulation. The impulse rate and wave form correspond to the rotational speed of manifold 3 and are adjusted at high volume section 35 of pump 21. Manifold 1, which is attached to base 80, has six outlet ports 31 through which the inlets 25 of sample test hoses 15 are attached.

Manifold 2 is slidably engaged into base 80. The six inlet ports 32 of manifold 2 are at right angles to the six outlet ports 31 of manifold 1. Because my invention can accommodate sample hoses of different diameter and length, the location of the manifold is adjusted prior to testing so that sample test hoses 15 undergoing the stationary-impulse test make a 90 degree bend between manifold 1 and manifold 2 in compliance with SAE J343. Manifold 2 is mounted on a slide 23. Once the correct position of manifold 2 is determined, the slide 23 is fixed in place and remains in that location for the duration of the testing procedure. When the testing system is activated, hydraulic oil at the desired temperature, impulse rate, and wave form is pumped through each sample test hose 15 for the requisite number of impulse cycles or until hose failure.

Manifold 3 also has a plurality of inlet ports 33 through which the outlets 26 of sample test hoses 15 are attached. Manifold 3 is attached to a slide 4 which in turn is attached to orbiter assembly 90. The orbiter assembly 90, which rotates manifold 3 in a plane parallel to that of manifold 1, moves manifold 3 in a continuous circular pattern. The diameter of the circular pattern can be varied by adjusting the manifold's position on slide 4 and by adjusting the length of the throw arms 8 and 9 of orbiter assembly 90. Each is adjusted such that the sample test hoses 15 extending between manifold 1 and manifold 3 flex through the required minimum and maximum bend radii during each revolution of the orbiter assembly 90.

The heated hydraulic oil flows through check valve 39 and heat exchanger 38 as it is returned to tank 20. If the temperature of the hydraulic oil exceeds the required temperature for the test, it is cooled by heat exchanger 38 before returning to tank 20 and being recirculated through the system.

Orbiter assembly 90, which is well known in the art, has a link arm 5 to which slide 4 is attached. Link arm 5 is a rectangular member having two apertures 16 and 17. Slide 4 is attached to one end of link arm 5; aperture 17 is located near the center of link arm 5; aperture 16 is located at the opposite end of link arm 5. Crank pins 10 and 11 pass through apertures 16 and 17 respectively. Crank pins 10 and 11 in turn pass through apertures 18 and 19 in crank arms 8 and 9 respectively. Crank arms 8 and 9 are also rectangular members whose lengths can be adjusted. The lengths of crank arms 8 and 9 must always be equal to insure that link arm 5 remains parallel to base 80. On their ends opposite aperture 18 and 19, the crank arms 8 and 9 are attached to reducers 12 and 13 at apertures 6 and 7. Reducer 12 contains both an input shaft 41 and an output shaft 42. Input shaft 41 is coupled to electric motor 14's output shaft 40 by couple 44. Output shaft 42 of reducer 12 is coupled to input shaft 43 of reducer 13 by couple 45. The reducer output shafts 46 and 47 to which the crank arms 8 and 9 are connected are at 90 degree angles to the reducer input shafts 41 and 43. When electric motor 14 is energized, reducers 12 and 13 reduce electric motor 14's rotational speed, increase its torque, and rotate crank arms 8 and 9 simultaneously at their predetermined radii. Link arm 5 rotates in a circular pattern around center points 6 and 7. Slide 4 and manifold 3 rotate in the same circular pattern whose plane is parallel to that of stationary manifold 1.

To perform the flex-impulse test on my invention, the position of manifold 3 with respect to manifold 1 is adjusted in compliance with SAE J1405. Each sample hose 15 tested must flex at a minimum and maximum radius with each revolution of the orbiter assembly 90. This is accomplished by adjusting the position of slide 4 and the lengths crank arms 8 and 9. Sample test hoses 15 are attached between manifold 1 and manifold 3. When the testing system is activated, manifold 3 rotates at 36±2% times the impulse rate of the hydraulic oil in cycles per minute. Hydraulic oil at the desired temperature, impulse rate, and wave form flows through each test hose as it is cycled through minimum and maximum bend radii by orbiter assembly 90 for the requisite number of impulse cycles or until hose failure.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A hydraulic hose tester comprising:
   a first manifold with a plurality of outlets and at least one inlet;
   a fluid pumping means for pumping fluid into the first manifold;
   the fluid pumping means being connected to an inlet of the first manifold by a first connecting means for discharging fluid from the fluid pumping means into the first manifold;
   a second manifold with at least one outlet and a plurality of inlets at predetermined angles from the plurality of outlets of the first manifold;
   a third manifold with at least one outlet and a plurality of inlets;
   the third manifold attached to a moving means for moving the third manifold in a predetermined path;
   a plurality of hydraulic connecting means for connecting at least one outlet of the plurality of outlets of the first manifold to at least one inlet of the second manifold and at least one other outlet of the plurality of outlets of the first manifold to at least one inlet of the third manifold.

2. The hydraulic hose tester of claim 1 further including a fluid intensification means for pressurizing fluid in the first manifold.

3. A hydraulic hose testing machine comprising:
   an inlet manifold having at least one inlet and a plurality of outlets;
   a first outlet manifold with at least one outlet and a plurality of inlets at predetermined angles from the inlet manifold;
   a second outlet manifold with at least one outlet and a plurality of inlets;
   the second outlet manifold attached to a moving means for moving the second manifold in a predetermined path;
   a fluid pumping means and a fluid connecting means for pumping and discharging fluid into at least one inlet of the inlet manifold;
   a plurality of hoses interconnected between at least one outlet of the inlet manifold and at least one inlet of the first outlet manifold and between at least one of the other outlets of the inlet manifold and at least one inlet of the second outlet manifold.

4. The hydraulic hose testing machine of claim 3 further including a fluid intensification means for pressurizing fluid in the inlet manifold.

5. The hydraulic hose testing machine of claim 3 further including adjusting means for adjusting the distance and angle between the inlet manifold and the first outlet manifold.

6. The hydraulic hose testing machine of claim 3 further including adjusting means for adjusting the distance and angle between the inlet manifold and the second outlet manifold.

7. The hydraulic hose testing machine of claim 3 in which the predetermined path of the second outlet manifold is a circle with a predetermined diameter.

8. The hydraulic hose testing machine of claim 3 further including heating and cooling means to heat and cool the fluid to a predetermined temperature.

9. A hydraulic hose testing machine comprising:
   a first manifold with at least one inlet and a plurality of outlets;
   a second manifold mounted at a predetermined angle to the first manifold with at least one outlet and a plurality of inlets;
   a third manifold with at least one outlet and a plurality of inlets;
   the third manifold attached to a moving means for moving the third manifold in a circular path of a predetermined diameter;
   a plurality of hoses each with two ends;
   the first end of at least one hose attached to at least one outlet of the first manifold and the second end attached to at least one inlet of the second manifold;
   the first end of at least one other hose attached to at least one other outlet of the first manifold and the second end attached to at least one inlet of the third manifold;
   a fluid pumping means for pumping fluid into the first manifold;
   the fluid pumping means being connected to at least one inlet of the first manifold by a connecting means for passing fluid from the pumping means to the first manifold.

10. The hydraulic hose testing machine of claim 9 further including a fluid intensification means for pressurizing fluid in the first manifold.

* * * * *